United States Patent [19]

Levenson

[11] Patent Number: 4,915,698
[45] Date of Patent: Apr. 10, 1990

[54] DEVICE FOR REMOVING AND REPLACING NEEDLE COVER ON SYRINGE

[76] Inventor: Myron F. Levenson, Timberidge Trail, Gates Mills, Ohio 44040

[21] Appl. No.: 216,777

[22] Filed: Jul. 8, 1988

[51] Int. Cl.[4] ............................................. A61M 5/32
[52] U.S. Cl. .................................. 604/192; 604/263; 128/919
[58] Field of Search .............. 604/192, 187, 263, 198, 604/110; D7/301; D8/18

[56] References Cited

U.S. PATENT DOCUMENTS

| | | | |
|---|---|---|---|
| D. 158,957 | 6/1950 | Haberkor et al. | D8/18 |
| D. 160,453 | 10/1950 | Ajouelo | D8/18 |
| 1,897,072 | 2/1933 | Parks et al. | D7/301 |
| 4,485,918 | 12/1984 | Mayer | 206/366 |
| 4,573,975 | 3/1986 | Frist et al. | 604/192 |
| 4,596,562 | 6/1986 | Vernon | 604/192 |
| 4,610,667 | 9/1986 | Pedicano et al. | 604/192 |
| 4,623,336 | 11/1986 | Pedicano et al. | 604/192 |
| 4,654,034 | 3/1987 | Masters et al. | 604/192 |
| 4,717,386 | 1/1988 | Simmons | 604/192 |
| 4,737,149 | 4/1988 | Gillihan | 604/192 |
| 4,852,844 | 8/1989 | Villaveces | 248/314 |

FOREIGN PATENT DOCUMENTS

| | | | |
|---|---|---|---|
| 2198644 | 6/1988 | United Kingdom | 604/192 |
| 2201094 | 8/1988 | United Kingdom | 604/110 |

Primary Examiner—C. Fred Rosenbaum
Assistant Examiner—Mark O. Polutta
Attorney, Agent, or Firm—D. Peter Hochberg; Mark Kusner; Louis J. Weisz

[57] ABSTRACT

A device for removing and replacing a protective cover on a needle of a hypodermic syringe. The device includes a base member having a generally planar bottom surface together with means for securing the bottom surface to an external flat surface. A tubular member extends from the base member at a predetermined angle relative to the planar bottom surface. The tubular member includes an open end for receiving axially a needle with a protective cover and an inner surface defining an elongated cylindrical cavity having an inner diameter sligthly larger than the maximum diameter of the protective cover to be received therein. Tab means extending inwardly from the inner surface of the tubular member are provided to operably engage a lip on the protective cover when the cover is within the cavity. The lip is operable to engage at the tab means when the protective cover is urged thereagainst whereby the protective cover remains within the tubular member while needle is removed therefrom. Reinsertion of the needle into the device replaces the protective cover thereon wherein the used needle may be safely disposed of or reused.

9 Claims, 3 Drawing Sheets

DEVICE FOR REMOVING AND REPLACING NEEDLE COVER ON SYRINGE

FIELD OF INVENTION

The present invention relates generally to medical appliances, and more particularly, to a device for preventing accidental needlesticks when removing and replacing a protective cover on a hypodermic needle.

BACKGROUND OF THE INVENTION

Hypodermic needles of the type used for injections or for drawing blood samples generally include a removable protective cover or cap which protects the needle and helps to keep it sterile in storage until used. It has become a conventional medical procedure to replace the cap on a used, "contaminated" needle ("recap") to prevent accidental needlesticks. In this respect, accidental needlesticks are a major concern in the medical field because they can spread infectious diseases, such as hepatitis, veneral diseases and AIDS. Nevertheless, accidental needlesticks occur quite often during recapping of used needles. In this respect it was reported at the Third International Conference on AIDS in Washington in June 1987 that 36% of the physicians training in internal medicine in New York City hospitals stated that they have accidentally stuck themselves with needles used on AIDS patients. Needlesticks have become such a major concern, that a division has been establish within the Hospital Infection Center at the Center for Disease Control to study needlestick cases.

Attempts to reduce the chance of accidental needlesticks have led to the development of devices such as those disclosed in U.S. Pat. Nos. 4,623,336 and 4,610,667 to Pedicano et al, U.S. Pat. No. 4,654,034 to Masters et al, and U.S. Pat. No. 4,573,975 to Frist et al. These devices generally relate to shields or funnel-shaped guards to protect the hand holding the protective cap during recapping. While these devices do provide greater protection for the user, they represent an increase in medical operating cost. In this respect, the disclosed devices relate either to a specific cap or cover design, or relate to a disposable holder suitable only for a single use. More importantly, however, each of these devices requires the use of two hands, i.e. one to hold the syringe with the needle, and the other to hold the cap or disposable shield. Use of these devices ultimately requires the used, contaminated needle to be moved toward another part of the body during recapping, specifically the hand holding the cap or sheath. With busy, rushed medical personnel (especially those who become too familiar with recapping procedures and/or those who rely too much on protective shields or funnels and therefore pay less attention when recapping the used needles), it will be appreciated that accidental needlesticks may still occur even with such devices. Any time a used, contaminated needle is being moved toward another part of the body, a slip of the hand, a bump, or a dropped syringe can result in an accidental needlestick.

The present invention overcomes these and other problems and provides an appliance for removing and replacing a protective cover on a syringe needle, which appliance does not require body parts to be in the vicinity of the used needle when recapping. Moreover, the appliance is quick and simple to use and is adapted for use with conventionally known protective needle covers.

SUMMARY OF THE INVENTION

The present invention finds advantageous application with protective caps or covers of conventionally known storage casings for hypodermic needles.

In accordance with the present invention, there is provided a device for removing and replacing a protective cover on a needle of a hypodermic syringe, the protective cover being of a type having an elongated generally cylindrical tubular body with a closed end, an open end for receiving the needle, and a lip or shoulder portion adjacent the open end. The device is comprised of a base member having a generally planar bottom surface and securing means for adfixing the bottom surface to a stationary flat surface. A tubular member extending from the base member is provided at a predetermined angle relative to the planar bottom surface. The tubular member includes an open end for receiving axially a protective needle cover and an inner surface defining an elongated cylindrical cavity having an inner diameter slightly larger than the maximum diameter of the protective needle cover to be received therein. Barrier means are provided within the cylindrical cavity a predetermined distance from the open end thereof to limit insertion of the protective needle cover into the cavity. Tab means extending inwardly from the inner surface of the tubular member are provided to operably engage the lip on the protective needle cover when the cover is within the cavity. The tab means restrict removal of the protective needle cover from the cavity when the protective needle cover is urged thereagainst. The tab means is dimensioned to allow insertion of the protective needle cover into the cavity when the cover is urged away from the tab means.

It is an object of the present invention to provide a medical appliance for safely removing and replacing the protectve cap or cover on the needle portion of a hypodermic syringe.

Another object of the present invention is to provide a medical appliance as described above which prevents accidental needlesticks by eliminating the exposure of body parts to the needle when the protective cap is removed or replaced.

Another object of the present invention is to provide a medical appliance as described above wherein replacement of the protective cap may be accomplished with one hand.

A still further object of the present invention is to provide a medical appliance as described above which permits repeated removal and recapping of the needle portion of the syringe.

A still further object of the present invention is to provide a medical appliance as described above which is adapted for use with conventionally known protective needle covers.

A still further object of the present invention is to provide a medical appliance as described above which appliance is simple, quick and easy to use.

These and other objects and advantages will become apparent from the following description of embodiments of the invention taken together with the accompanying drawings.

The invention may take physical form in certain parts and arrangements of parts, embodiments of which are described in detail in the specification and illustrated in the accompanying drawings wherein.

DETAILED DESCRIPTION OF THE PREFERRED EMBODIMENT

Figure 1:
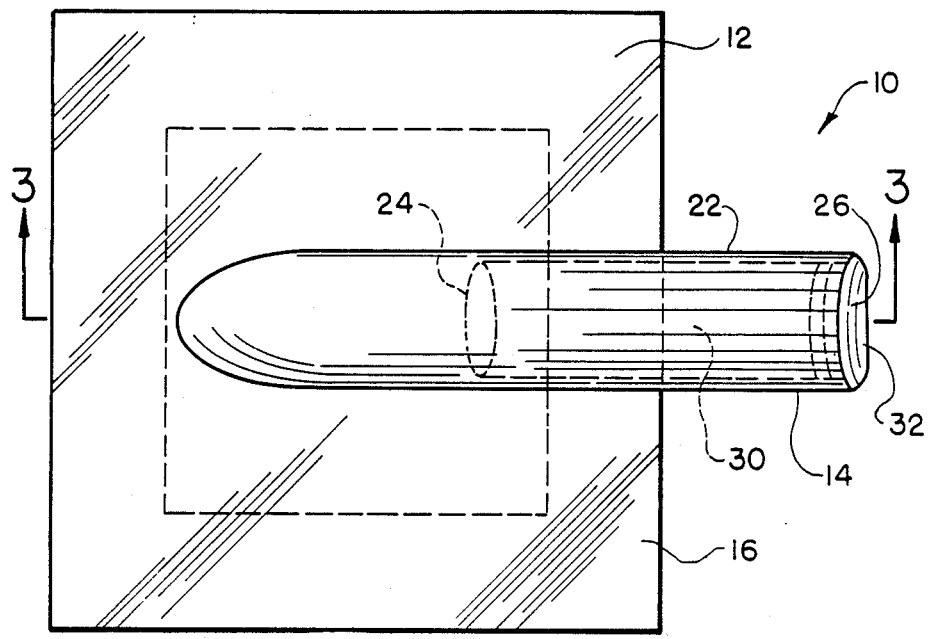
FIG. 1 is a top, plan view of a device for removing and replacing a protective cover for a hypodermic needle illustrating a preferred embodiment of the present invention.
Figure 3:
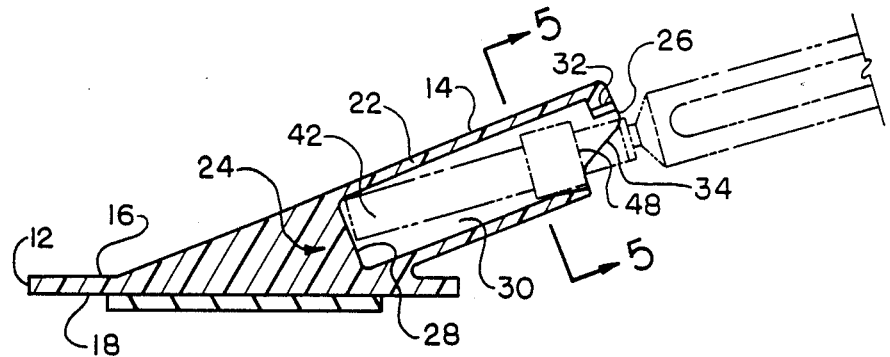
FIG. 3 is a sectional, side elevational view taken along line 3—3 in FIG. 1 showing a syringe (in phantom) having a protective needle cover in place being inserted into the device.
Figure 4:
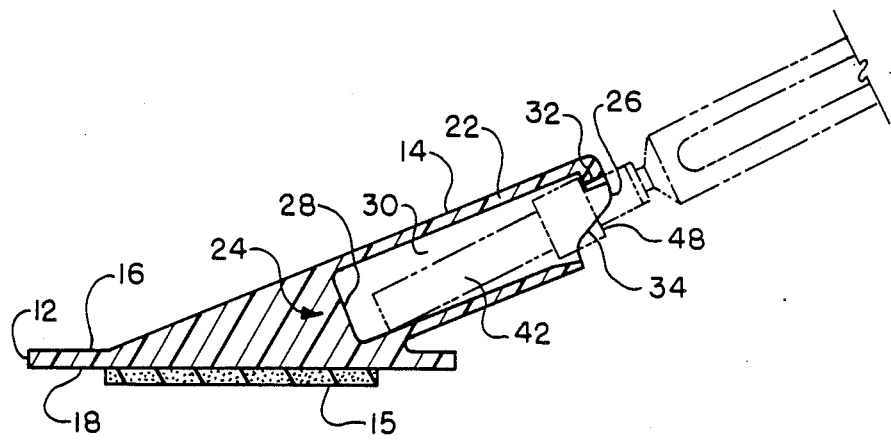
FIG. 4 is a view of the section shown in FIG. 3 showing the needle cover (in phantom) being removed from the syringe.
Figure 5:
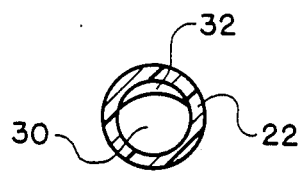
FIG. 5 is a sectional view taken along lines 4—4 of the FIG. 3.

Referring now to the drawings wherein the showings are for the purpose for illustrating a preferred embodiment of the invention, and not for the purpose of limiting same. FIG. 1 illustrates a device designated 10 for removing and replacing a protective cover for a hypodermic needle. Device 10 is comprised of a base portion 12 and a tubular portion 14 extending therefrom. In the embodiment shown, base portion 12 is generally rectangular and includes an upper surface 16 and a planar, lower surface 18 (FIG. 3). Tubular portion 14 includes a cylindrical wall 22 and has a closed end 24 and an open end 26. In the embodiment shown, tubular portion 14 is integrally formed with base portion 12 and extends therefrom at a predetermined angle relative to lower surface 18. Device 10 may be formed from a metallic material or molded from a hard durable plastic material. Closed end 24 is formed to define a wall portion 28 (FIG. 3) spaced a predetermined distance from open end 26. The distance between wall portion 28 and open end 26 is related to the length of the needle cover to be used therein as will hereinafter be described. Cylindrical wall 22 and end wall 28 define a cylindrical cavity 30 of predetermined length and diameter. A tab or lip 32 extending inwardly from cylindrical wall 22 is provided at open end 26 (FIG. 5). A portion of cylindrical wall 22 opposite tab 32 is removed to define a recess 34, as best seen in FIGS. 3 and 4. Device 10 is adapted to be attached to a stationary planar surface, such as a counter top or the like. In the embodiment shown, a strip 15 of a double-sided, adhesive foam material is attached to planar surface 18. The adhesive strip is of a type having sufficient holding power to enable use of device 10 as hereinafter described.

Figure 2:
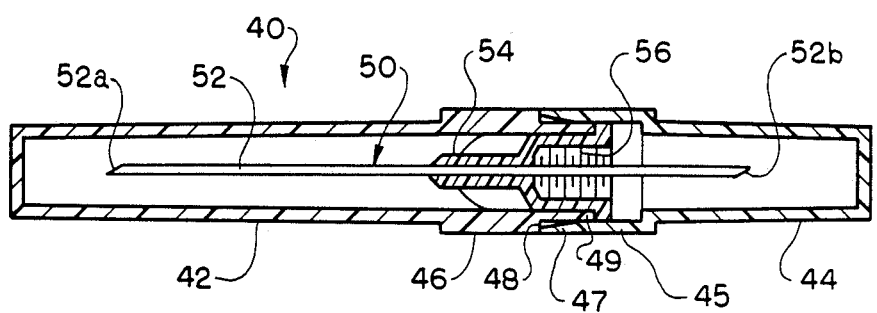
FIG. 2 illustrates a conventionally known casing containing a hypodermic needle.

Referring now to FIG. 2, a conventionally known casing designated 40 for a hypodermic needle 50 is shown. Casing 40 in and of itself forms no part of the present invention, but will be described to illustrate application and use of the present invention. In this respect, casing 40 is representative of the typical means for storing and protecting hypodermic needle 50 until use. In this respect, hypodermic needle 50 is generally comprised of a long, very slender tubular portion 52 having a pointed end 52a operable to penetrate body tissue, and a portion 52b adapted to extend into the piston portion of a syringe. Tubular portion 52 extends through a ferrule 54 which is attachable to the syringe by means of threads 56. Hypodermic needle 50 is stored in casing 40 to protect the needle and to prevent contamination until use. Casing 40 is generally comprised of a first cover section 42 operable to protect the operative end 52a of the hypodermic needle 50, and a second cover section 44 which protects portion 52b which attaches to the syringe. Cover section 42 includes an enlarged area 46 which defines a shoulder 48 and a tubular extension 49, as shown in FIG. 2. Cover section 44 includes a sleeve portion 45 having an end surface 47. Sleeve portion 45 of cover section 44 is dimensioned to receive extension 49 of cover section 42 wherein end surface 47 abuts shoulder 48.

When a hypodermic needle 50 is needed for an injection or to draw blood, cover section 44 is separated from cover section 42 to expose the syringe portion 52b of the needle. (Cover sections 42, 44 are generally secured to each other to prevent separation until initially used. Separation is normally accomplished by twisting one cover section relative to the other). Using threads 56, a syringe body is attached to the needle while cover section 42 is maintained in position over end 52a to maintain sterile conditions, and at the same time, to protect the individual assembling the syringe. Thus, the syringe is assembled while the needle cover section 42 is still in position over needle portion 52a.

Referring now to the operation of device 10, cover section 42 may be removed from the syringe without the necessity of the individual to physically grab cover section 42. In this respect, FIG. 3 illustrates the position of a needle section cover 42 attached to a syringe inserted into cavity 30 of device 10. By tilting the syringe downward towards base portion 12, i.e. moving area 46 on cover section 42 away from tab 32, the needle cover may be inserted within the cavity 30. Wall 28 limits the travel of the cap into device 10. To remove the cover section 42, the individual need only tilt the syringe and cover section 42 upwardly toward tab 32 to the position shown in FIG. 4. In this position, tab 32 engages shoulder 48 on cover section 42 and maintains cover section 42 within the cylindrical cavity 30 as the syringe is withdrawn therefrom. Once the needle 50 has been withdrawn from the cover section 42, cover section 42 settles within cavity 30 and is retained therein. To recap the hypodermic needle 50 after use, the individual need only direct tubular portion 52a back into cover section 42 and to force the same back on to ferrule 54. In this respect, end wall portion 28 limits movement of cap 42 into cavity 30. Once cap 42 is secured on ferrule 54, the syringe and cover section 42 may be withdrawn from device 10 by tilting the axis of the assembly downward, i.e. away from tab 32, and withdrawing cover section 42 from cavity 30.

It will thus be appreciated that the present invention provides a device wherein a cap can be removed and replaced on a hypodermic needle without the necessity of an operator holding the cap, thereby avoiding the likelihood of accidental needlesticks. The device provides a simple, easy to use device wherein removal and replacement of the cap can be accomplished with one hand. More importantly, the device maintains the cap in a specific location, i.e. within cavity 30, while the syringe is in use, such that the doctor, dentist or nurse need not hunt for the cover on a cluttered table top or tray, which is presently a real problem. Moreover, the present invention enables repeated use of the same needle when repetitive injections on the same patient may be necessary. In this respect, the present invention provides a simple, easy to use device which finds advantgeous application in all medical fields using hypodermic needles.

Figure 6:
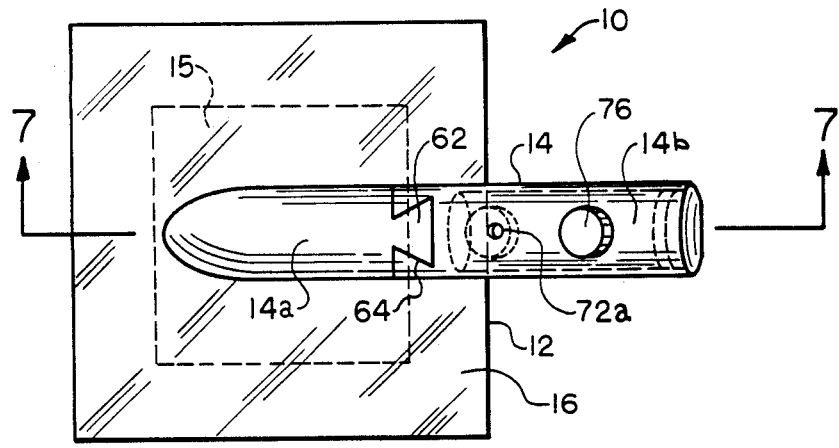
FIG. 6 is a top, plan view of a device for removing and replacing a protective cover on a hypodermic needle illustrating another embodiment of the present invention.
Figure 7:
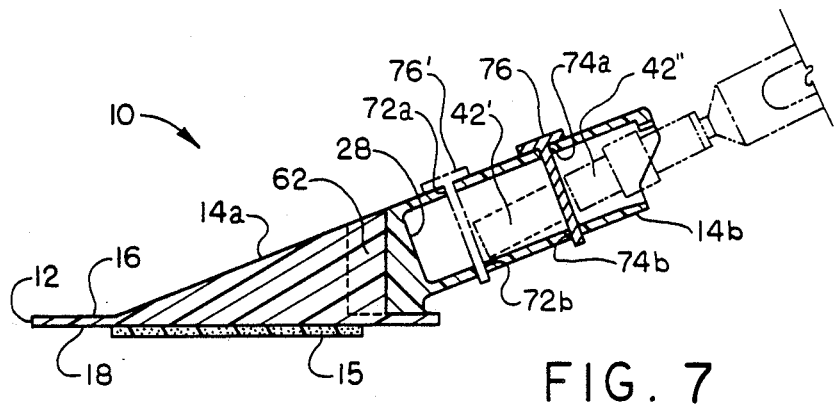
FIG. 7 is a sectional view taken along line 7—7 of FIG. 6 showing a syringe in phantom.
Figure 8:
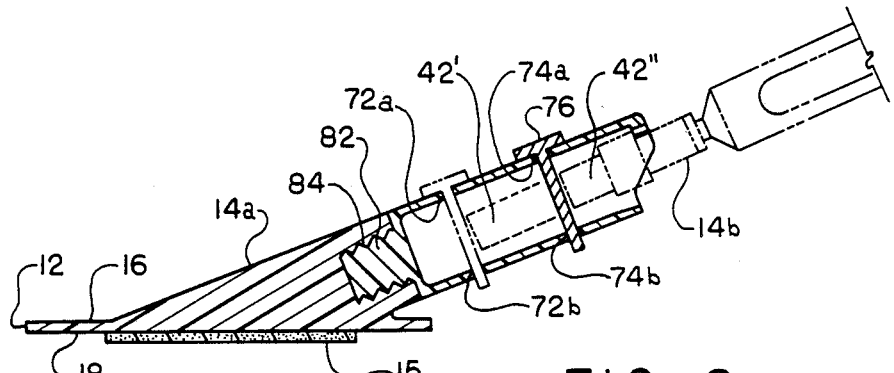
FIG. 8 is a sectional view of a device for removing and replacing a protective cover on a hypodermic needle illustrating an additional embodiment of the present invention.

Referring now to FIGS. 6–8, alternate embodiments of the present invention are shown. In these figures, many elements of the devices correspond to parts previously described with respect to the embodiment shown in FIGS. 1–5. Like elements have been designated with like numbers, and will be described only when necessary for an understanding of the alternate embodiments. Components modified from corresponding components in FIGS. 1–5 have been ascribed a prime (') designation.

FIGS. 6 and 7 show a device 10' for removing and replacing a protective cover for a hypodermic needle, which device includes means for removing the operative segment of tubular portion 14' from base portion 12, and means for adjusting the axial length (i.e. depth) of cavity 30. In this respect, tubular portion 14' is comprised of two distinct, separable sections, 14a, 14b. In the embodiment shown, section 14a is integrally formed with base portion 12 and includes a dovetail-shaped projection 62 at the end thereof. Section 14b which includes cavity 30, has a dovetail-shaped groove 64. Groove 64 is dimensioned to matingly receive projection 62 in a manner as is conventionally understood. In this respect, section 14b is removable from base portion 12 for cleaning, sterilization, or even replacement by another section.

Because hypodermic needles come in various lengths, and the covers which protect them are dimensioned accordingly, section 14b includes aligned pairs of apertures 72a, 72b, and 74a, 74b, which extend through wall 22 transversely through the axis of cavity 30 as best seen in FIG. 7. Each pair of apertures 72a, 72b and 74a, 74b is dimensioned to receive a pin 76 therein. FIG. 7 shows pin 76 disposed within aperture 74a, 74b. In this position, pin 76 effectively shortens the usable, axial length of cavity 30. In other words, the end of a cover section would engage pin 76 and "bottom-out" at that position instead of at wall portion 28. Such modification to the length of cavity 30 finds advantageous application when recapping short needles having short cover sections thereon. Such shorter cover section could not be fully inserted into cavity 30 for the end thereof to engage wall portion 28. To illustrate this condition, two cover sections 42' and 42" of different length are shown inphantom in FIGS. 6 and 7. The end of cover section 42' would engage pin 76 at the position shown in the figures, when pin 76 extends through apertures 72a, 72b. In a similar manner, the shorter cover section 42" would engage pin 76 when pin 76 extends through apertures 74a, 74b. Thus, there is provided a device for removing and replacing a protective cover from a hypodermic needle, which device is adaptable for use with needles (and covers) of varying lengths. It will, of course, be appreciated that the position, spacing and number of pairs of apertures provided in section 14 may vary depending upon the application and use of the device.

FIG. 8 discloses another embodiment of the present invention showing another manner in which section 14b may be attached to section 14a. In this embodiment, a threaded extension 82 is provided on section 14b to be received in mating fashion with a threaded bore 84 in section 14a.

The present invention has been described with respect to preferred embodiments. Modifications and alterations will occur to others upon their reading and understanding of the specification. It is intended that all such modifications and alterations be included insofar as they come within the scope of the patent as claimed or the equivalents thereof.

Having described the invention, the following is claimed:

1. A needle cover removing and replacing device for removing and replacing a cover on a needle of a syringe, said cover having an elongated, generally cylindrical tubular body and including a closed end, an opened end for receiving said needle and a lip adjacent the open end, said device comprising:

a securable surface for being secured to a separate surface, a generally hollow member having an open end dimensioned to receive axially a needle cover, and an inner surface defining an elongated cavity having an inner transverse dimenson slightly larger than the maximum diameter of said needle cover to be received therein;

barrier means within said cavity a predetermined distance from said open end to limit receipt of said cover within said cavity; and tab means extending inwardly from said inner surface of said hollow member, said tab means being dimensioned to allow insertion of said cover into said cavity when said cover is urged away therefrom and said tab means being operable to engage said lip on said cover when said cover is within said cavity and to restrict removal of said cover therefrom when said cover is urged thereagainst, said cover being retained in said cavity after removal from said syringe when said syringe is drawn away from said device.

2. A device as defined in claim 1, wherein said securable surface, said hollow member, and said tab means are integrally formed of a plastic material.

3. A device as defined in claim 1 wherein said securable surface includes a securing means comprised of double-side adhesive foam tape.

4. A device as defined in claim 1 wherein said barrier means is positionable axially within said cavity to vary said predetermined distance.

5. A device as defined in claim 1 wherein said hollow member is removable from said securable surface.

6. A device as defined in claim 1 wherein said hollow member includes means for varying the length of said elongated cavity.

7. A device as defined in claim 6 wherein said means for varying the length of said elongated cavity is comprised of aperture means extending through said hollow member and a pin extending through said aperture means in the path of a needle cover inserted into said cavity.

8. A device as defined in claim 1 wherein said securing means comprises means for affixing said securable surface to a separate stationary surface.

9. A device as defined in claim 1 wherein said cavity is cylindrical.

* * * * *